US005763768A

United States Patent [19]

Henderson et al.

[11] Patent Number: 5,763,768
[45] Date of Patent: Jun. 9, 1998

[54] ANALYTICAL METHOD USING MODIFIED SCANNING PROBES

[75] Inventors: Eric R. Henderson; Curtis L. Mosher; Vivian Wynne Jones, all of Ames, Iowa; John-Bruce D. Green, Alexandria, Va.; Marc D. Porter, Ames, Iowa

[73] Assignee: Iowa State University Research Foundation, Inc., Ames, Iowa

[21] Appl. No.: 819,667

[22] Filed: Mar. 17, 1997

[51] Int. Cl.⁶ .............................. G01B 5/28; G01N 33/50
[52] U.S. Cl. ............................................................ 73/105
[58] Field of Search ............................ 73/105; 250/306, 250/307

[56] References Cited

U.S. PATENT DOCUMENTS

| 5,047,633 | 9/1991 | Finlan et al. | 250/306 |
| 5,363,697 | 11/1994 | Nakagawa | 73/105 |
| 5,372,930 | 12/1994 | Colton et al. | 250/306 X |
| 5,519,212 | 5/1996 | Elings et al. | 73/105 X |
| 5,624,845 | 4/1997 | Wickramasinghe et al. | 250/306 X |

FOREIGN PATENT DOCUMENTS

| 2235049 | 2/1991 | United Kingdom | 73/105 |

OTHER PUBLICATIONS

Erlandsson et al., "Scanning Force Microscopy—Examples of Applications to Surface Chemistry", received Jun. 1992, pp. 1–21.

Nakagawa et al., "Discriminating Molecular Length of Chemically Adsorbed Molecules Using an Atomic Force Microscope Having a Tip Covered with Sensor Molecules (An Atomic Force Microscope Having Chemical Sensing Function)", Jpn. J. Appl. Phys., vol. 32, P.

*Primary Examiner*—Hezron E. Williams
*Assistant Examiner*—Daniel S. Larkin
*Attorney, Agent, or Firm*—Henderson & Sturm

[57] ABSTRACT

The present invention provides a method of analyzing for a specific material in a sample using a sensor including a resonating member having resonating properties. The resonating member has a probe and a known material is disposed on or forms the probe. The method includes the steps of positioning the sensor proximate to the sample, detecting a force dependent change in the resonance properties of the sensor, and confirming the presence of the specific material based on the identity of the known material and the detection of a resonance change.

25 Claims, 15 Drawing Sheets

Antibody

Fluorescent primary (middle panel) or secondary (right panel) antibody.

5,763,768

ANALYTICAL METHOD USING MODIFIED SCANNING PROBES

AUTHORIZATION PURSUANT TO 37 C.F.R. §1.71 (d) (e)

A portion of the disclosure of this patent document, including appendices, may contain material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to analyses for specific materials and, more particularly, to an analytical method using chemically and biologically modified scanning probes.

2. Description of the Related Art

The numbers in brackets below refer to references listed in the Appendix, the teachings of which are hereby incorporated by reference.

Detection of interactions between biological molecules is the basis for a large number of assays in biomedical diagnostics and basic and applied biomolecular research. Most of these assays are diffusion limited, requiring relatively large populations of molecules, and reporter systems involving chemical, enzymatic, or radioactive components.

The recent development of scanning probe detection instrumentation, in particular the atomic force microscope (AFM) (1), opens the door to a new era of molecular detection. In the AFM, a sharp stylus (the scanning tip) is present at the end of a flexible cantilever. The tip is scanned over a sample and deflections of the cantilever result from force interactions between the tip and a substrate. Since the spring constant of the cantilever is known, these forces can be accurately determined, monitored, and controlled. Cantilever deflection is usually measured by a laser system in which a beam is reflected from the back of the cantilever onto a split photodiode, constituting an "optical lever" or "beam deflection" mechanism (2-4). Other methods for detecting cantilever deflection include interferometry and piezoelectric strain gauge systems. The interferometer approach uses a small light source placed very close to the cantilever. Variation in the interference between the incident and reflected beams report cantilever motion. Piezoelectric strain gauge systems incorporate a piezoelectric (or piezoresistive) device in the cantilever itself. As the cantilever bends a signal is generated, thereby reporting interactions between the scanning tip and the sample.

The AFM is extraordinarily sensitive, being capable of detecting force interactions between individual molecules, chemical groups and even single quantized hydrogen bonds. Specific examples include: avidin/biotin interactions (5-7), DNA—DNA interactions (8, 9), antibody-antigen interactions (10), chemical group interactions (11-13), and individual hydrogen bonds (14). These proof of principle experiments were performed using specially modified scanning tips and monitoring force interactions between the modified tip surface and defined substrates. In most cases, the tip was placed on the surface and then pulled away. The adhesive force resulting from interactions between the modified tip and the surface was monitored and quantitated based on the force generated. In a minority of instances, lateral forces (i.e., friction), rather than vertical forces were measured, again as the result of specific tip-surface interactions. None of these experiments utilized a resonating probe, which is the emphasis of this application. In the patent awarded to Elings et al., U.S. Pat. No. 5,025,658 issued Jun. 25, 1991, use of a resonating probe is mentioned but no experimental evidence of this approach is presented. We present here direct experimental evidence that a resonating probe approach can be employed to detect specific molecular interactions. This is presented in the form of a molecular force immunoassay. Furthermore, we present reliable methods for production and testing of modified AFM probes, information lacking in the prior art. The information presented herein is novel and not obvious, and, therefore, appropriate for patent protection.

Those concerned with these and other problems recognize the need for an improved analytical method using modified scanning probes.

BRIEF SUMMARY OF THE INVENTION

The present invention provides a method of analyzing a specific material in a sample using a sensor including a resonating member having resonant properties. The resonating member has a probe and a known material is disposed on or forms the probe. The method includes the steps of positioning the sensor proximate to the sample, detecting a force dependent change in the resonant properties of the sensor, and confirming the presence of the specific material based on the identity of the known material and the detection of a resonance change.

An object of the present invention is the provision of an improved analytical method using a modified scanning probe similar to that used in the atomic force microscope.

BRIEF DESCRIPTION OF SEVERAL VIEWS OF THE DRAWINGS

Other objects, advantages, and novel features of the present invention will become apparent from the following detailed description of the invention when considered in conjunction with the accompanying drawings, wherein.

DETAILED DESCRIPTION OF THE INVENTION

The following examples are illustrative of the best mode for carrying out the invention. They are obviously not to be construed as limiting the invention since various other embodiments can readily be evolved in view of the teachings provided herein.

Figure 1:
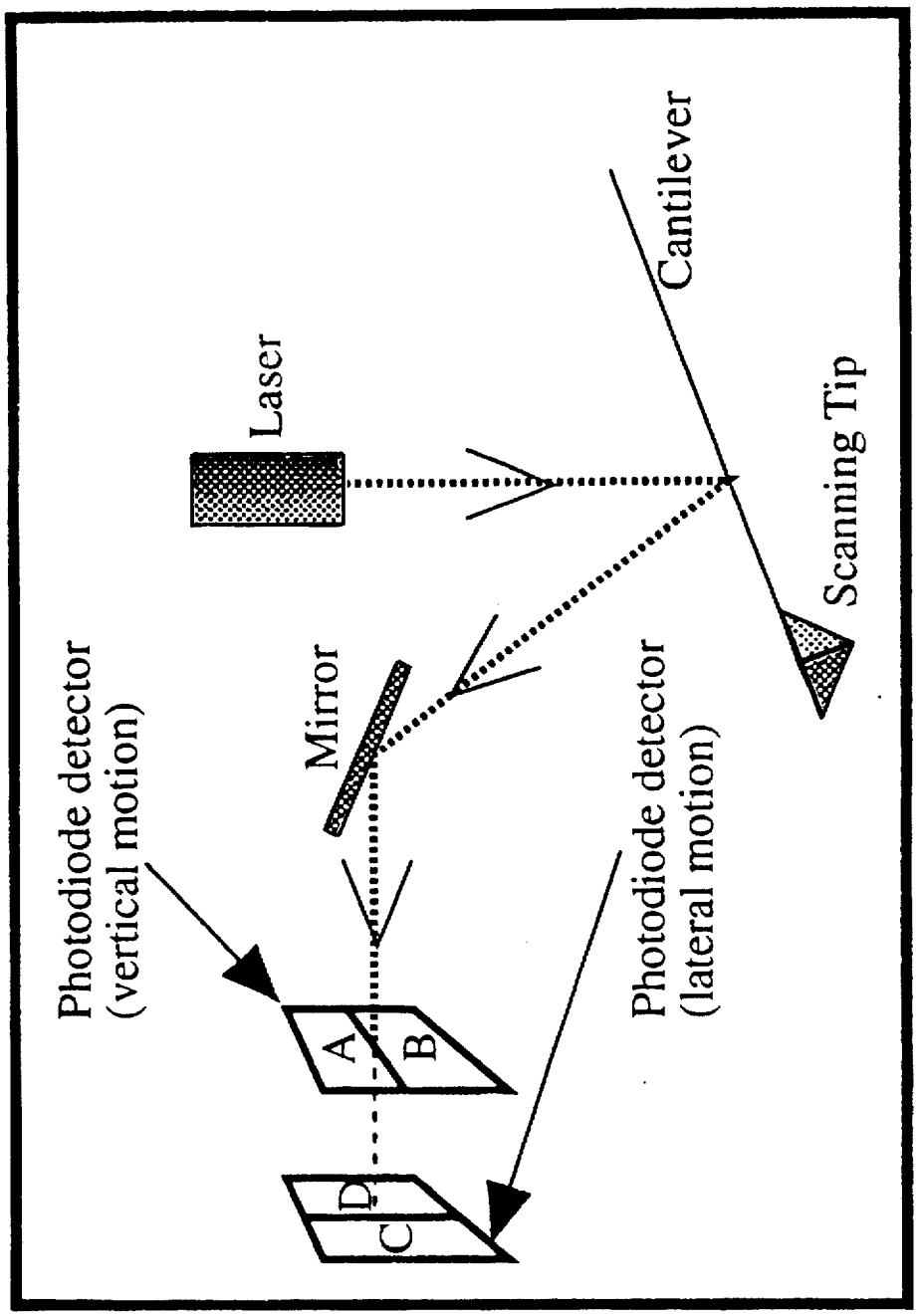
FIG. 1 is a schematic illustrating the operation of an atomic force microscope having a cantilevered probe.

As shown in FIG. 1, the cantilever of the atomic force microscope is traced over a sample of interest. Deflections in the cantilever result in movement of a laser beam impinging on a photodiode. This results in a change in the output voltage from the photodiode which is proportional to the amount of deflection of the cantilever. This change can be used as a measure of the topography of the sample or of other tip sample interactions.

Several methods for modification of scanning probes are shown in FIGS. 3–7. The attachment of virtually any protein, nucleic acid or other biomolecule, or chemical group to the scanning tip is possible. Modified tips such as these can then be used to detect interactions between the molecules on the tips and on surfaces, as depicted for an antibody interaction in FIG. 2.

Experimental Design and Methods

TEST SYSTEMS

A variety of molecular pairs can be used in the molecular detection system described herein. Some representative examples are listed in Table 1. Some of the molecular pairs listed in Table 1 have been tested by other groups but have not been evaluated using the modified scanning probes and methods described here. They will be useful in comparing reproducibility and reliability of the different systems. Other molecular pairs have not been tested but are important for diagnostic applications. As representative examples of test cases we present data describing molecular force detection using an antibody-antigen system, and supportive data using a protein-DNA system. The antibody system is a "sandwich" type assay in which the antigen is trapped between two antibodies. In our implementation, one antibody is immobilized on a solid surface, and the second is attached to the probe. When the antigen is introduced, it is trapped between the two antibodies, forming a trimolecular complex. The force necessary to rupture this complex provides the macroscopic signal, in the form of a direct force measurement or, more pertinent to this application, in the form of a change in a resonance property of the probe. The protein DNA system includes a recombinant yeast transcription factor, Gal 4, and its target DNA duplex sequence In this assay, the Gal 4 protein is attached to the probe, and the DNA target is attached to a solid surface. The interaction between the protein and the DNA is detected and measured as described above for the antibody-antigen interaction.

TABLE 1

| Interaction Type | Molecular Pair |
|---|---|
| DNA/DNA | oligo d(T)/d(C), d(ACTG)n/e(CAGT)n |
| Protein/DNA | Anti-DNA/DNA |
| | Protein/DNA |
| | Gal4/Gal4 binding domain |
| Receptor/Ligand | NMDA Receptor/conatokin-G |
| Protein/Protein | antibody-antigen-antibody sandwich |
| | Anti-streptavidin/streptavidin |

TIP MODIFICATION METHODS

Tip Modification and Modification Efficiency

Several methods are used to construct modified scanning probes. These can be subdivided into two classes: direct attachment to the existing tip, and attachment of a functionalized particle to the cantilever. In this application we describe two methods that have been fully developed and evaluated in terms of tip function and maintenance of biological activity. These methods include attachment of microparticles to tips and coating tips with a chemically reactive monolayer, which is then covalently bonded to molecular species. Other methods have been tested and are described briefly below.

Passive Adsorption

Passive adsorption is the simplest attachment method. This method has been used successfully for attachment of biotinylated BSA to scanning tips which were used to measure avidin-biotin interactions (5, 7, 9). The method of attachment is to simply immerse a tip into a solution of the molecule of interest. Molecules become adsorbed to the surface through non-covalent interaction, but these interactions can be very strong, in some cases, functionally irreversible. After adsorption, loosely bound molecules are removed by extensive washing. Despite its successful use in some experiments, significant tip degradation was observed with the passive adsorption method. Therefore, we have not pursued this method.

Figure 3:
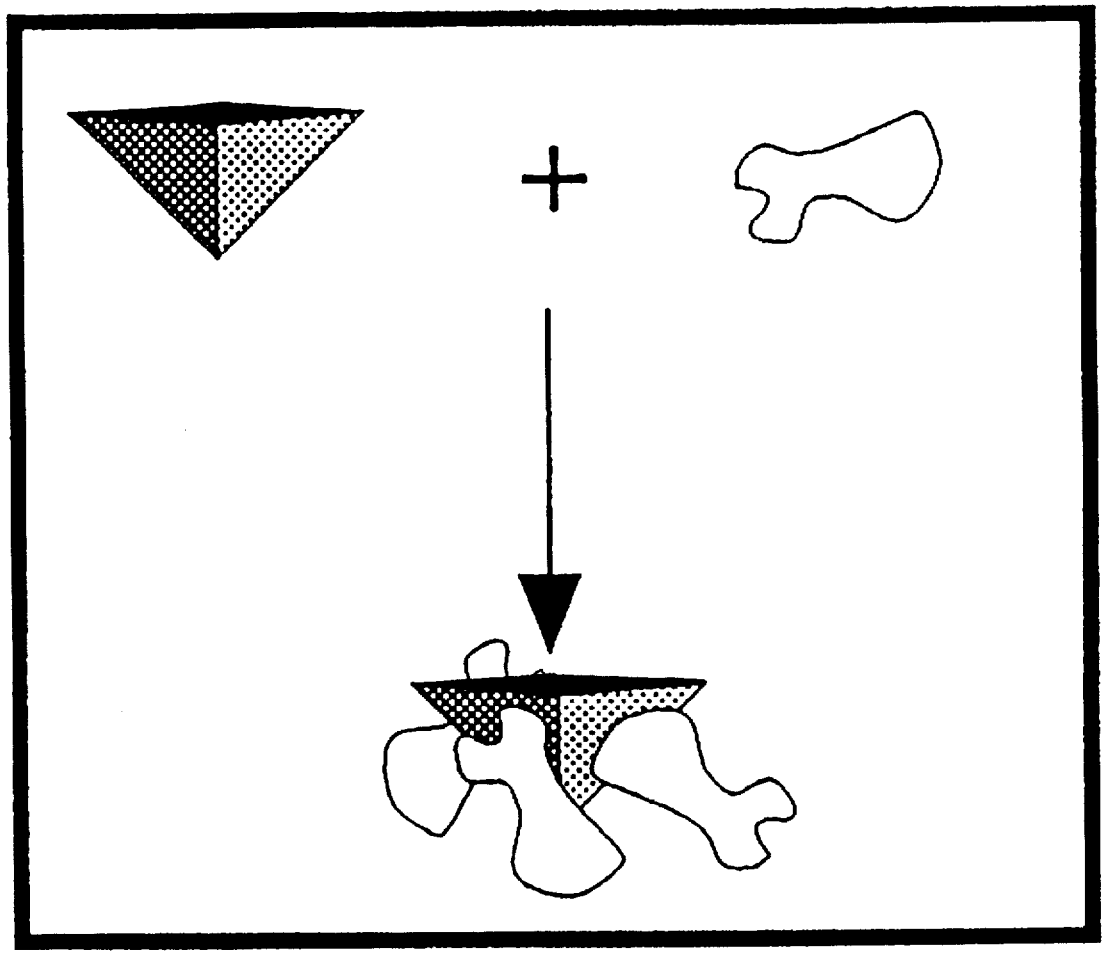
FIG. 3 is a schematic illustrating the modification of a scanning tip by passive adsorption of a biomolecule.

FIG. 3 schematically illustrates modification of a scanning tip (pyramid) by passive adsorption of a biomolecule. The tip is submerged in a solution of the molecule of interest and adsorption of the molecule to the tip surface proceeds spontaneously. Loosely bound molecules are removed by extensive washing, leaving behind only those molecules that are tightly bound to the tip surface.

Adhesive Protein Facilitated Attachment

Recent work has shown that the marine muscle adhesion protein ("Cell-Tak", Collaborative Biomedical Products; J. Hoh, personal communication) greatly facilitates binding of materials to surfaces for imaging in the AFM. In these experiments, the surface is coated first with Cell-Tak, rinsed well, then incubated with the sample of interest. In tests of tips constructed this way, appropriate negative controls are included to ensure that any tip/sample interaction observed is not the result of non-specific interactions between the Cell-Tak and the surface under scrutiny. This method ultimately relies on the poorly characterized adsorption forces between the adhesive layer and the tip, and between the adhesive layer and the molecular species of interest. This method has not been pursued further.

Gold/Alkanethiolate Adsorption

Figure 4:
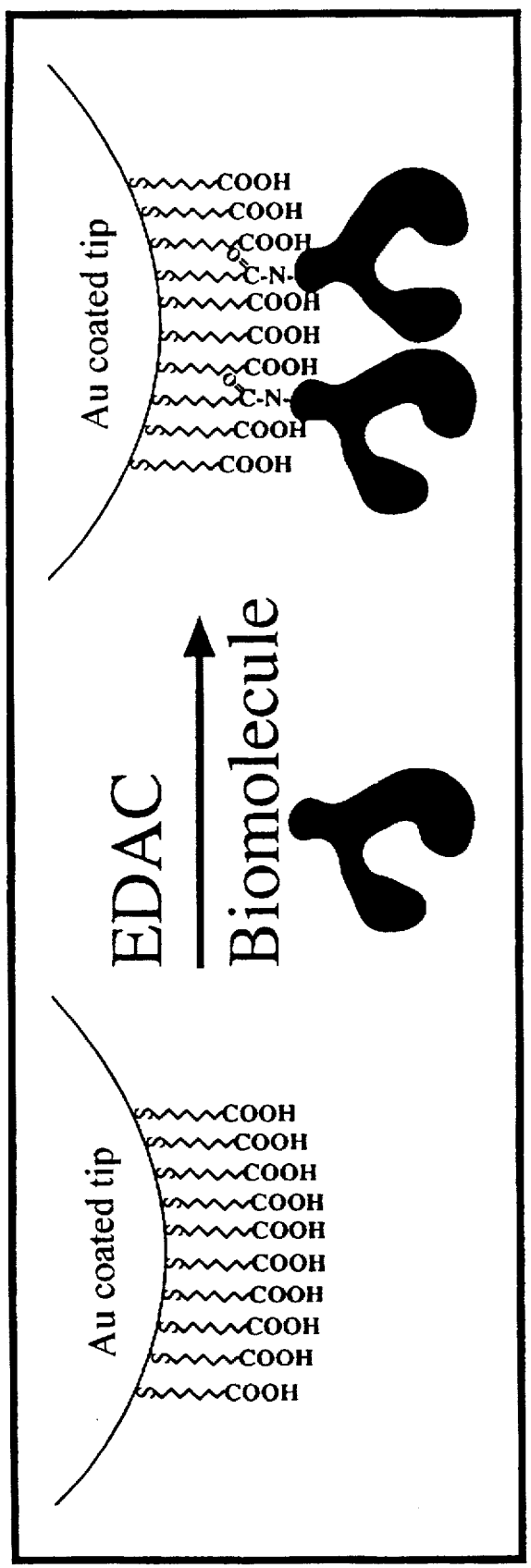
FIG. 4 is a schematic showing the alkanethiolate method of attachment of proteins to a gold coated tip.
Figure 11:
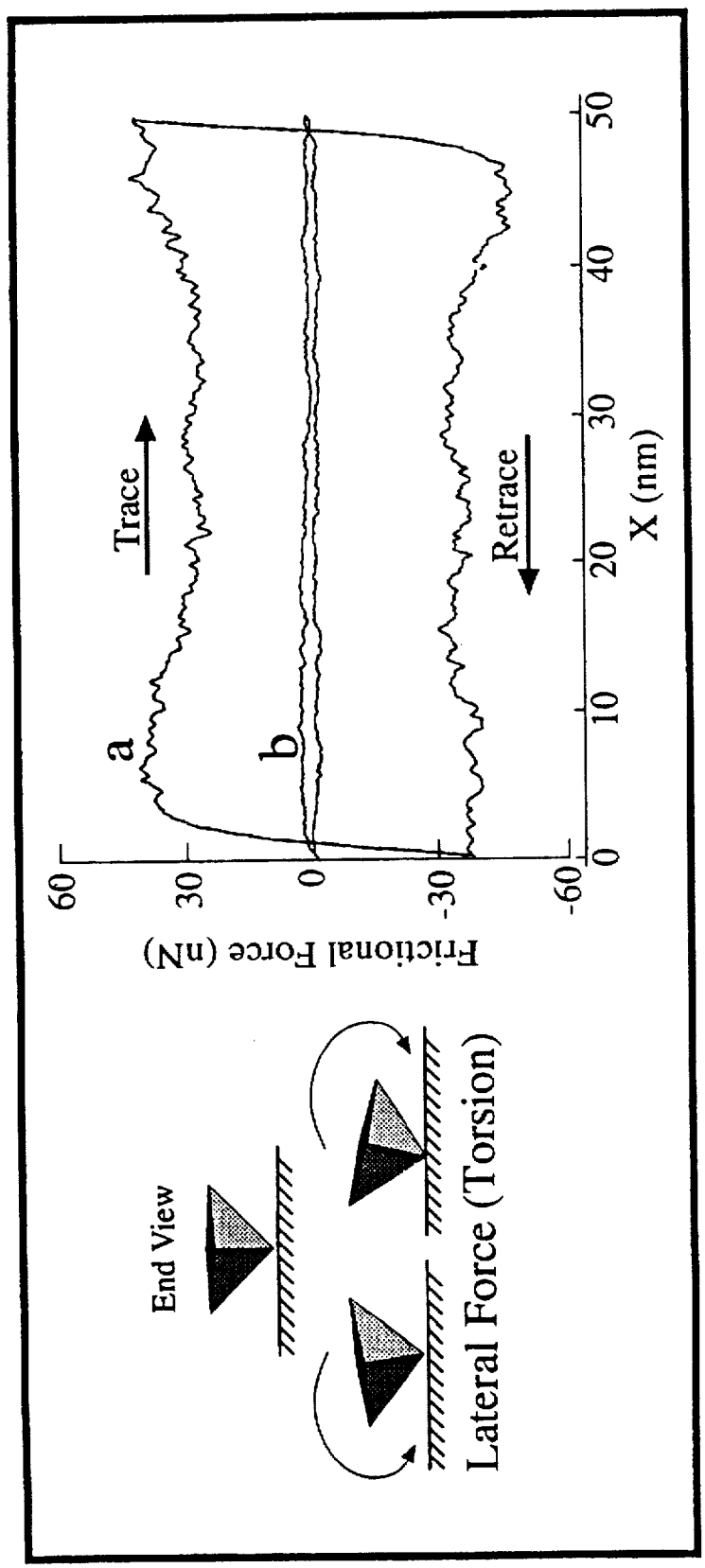
FIG. 11 is a schematic showing lateral force and resonance-based measurements.

The non-covalent bond formed between gold and sulfur is very strong, approximating the strength of a covalent bond. Moreover, when many alkanethiolate molecules are bonded to a gold surface, they pack in an ordered array, providing increased stability and strength. We have exploited these observations in the construction of robust modified tips. Tips are coated with gold using an ion beam sputter or vacuum evaporator. An alkanethiolate is then adsorbed to the tip, forming a monolayer. In initial studies, the alkanethiolate had a carboxyl group at the free terminus which was then linked to the biomolecule of interest using a carbodiimide such as EDAC, [1-ethyl-3(3-dimethylaminopropyl) carbodiimide] (See FIG. 4). Tips and substrates prepared in this way have proven successful for molecular detection in antibody sandwich assays (FIG. 11). Additional experiments are carried out with different terminating chemical groups (amino, azido) to facilitate coupling of biomolecules to tips. The wide spectrum of possible terminating groups makes this system particularly attractive for the creation of modified scanning probes with diverse functional characteristics. In the case of oligonucleotides, thiol groups are incorporated during the synthesis using phosophorothioate nucleotides at either the 3' or 5' end. These thiol modified oligonucleotides are then adsorbed to the gold surfaces (tips and substrates) in the same fashion as the alkanethiolates. FIG. 4 schematically illustrates the alkanethiolate method for attachment of proteins to gold coated tips and surfaces.

Direct Covalent Attachment

Figure 5:
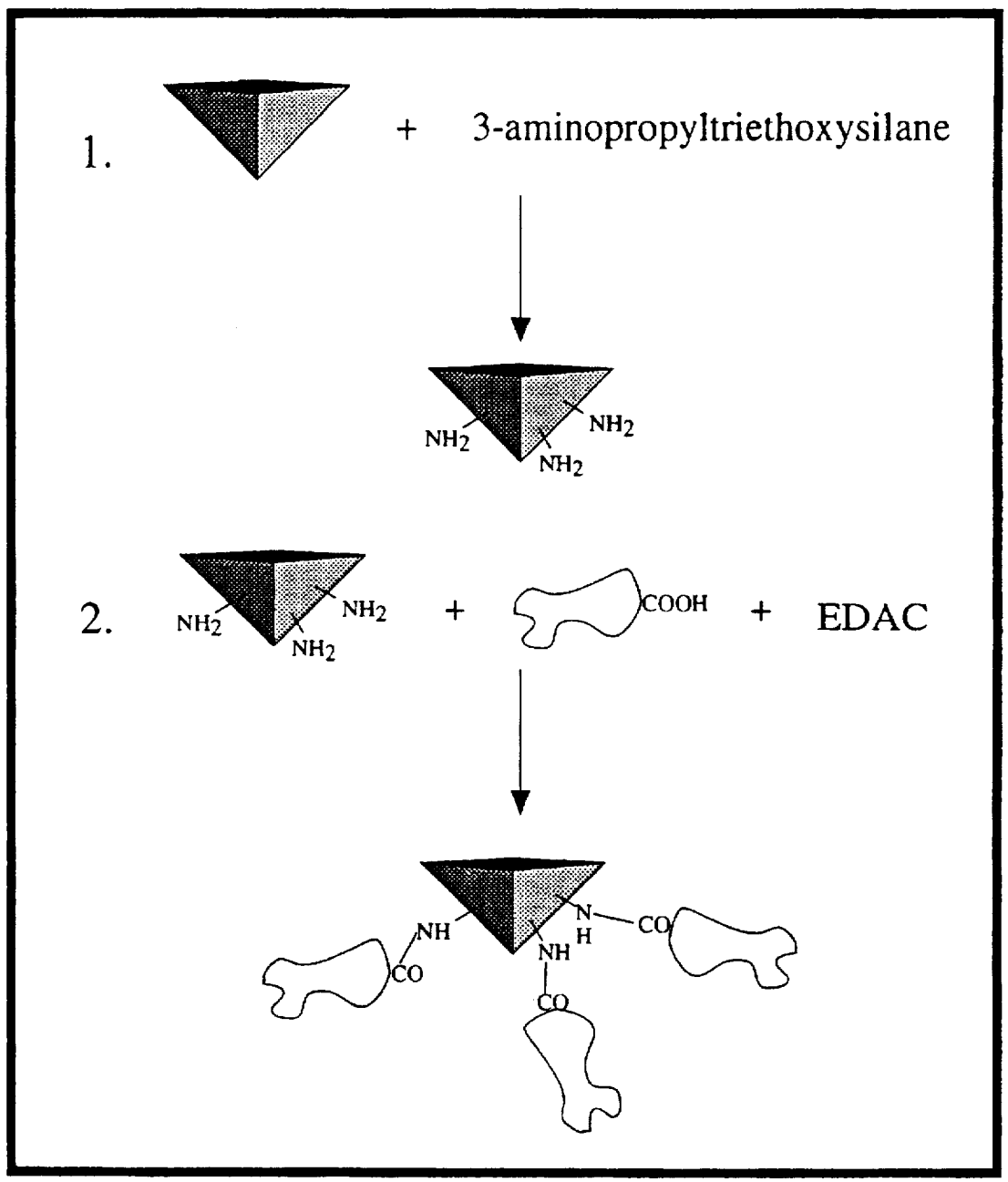
FIG. 5 is a schematic showing covalent attachment of biomolecules to a tip.

Direct covalent attachment uses various silane compounds (See FIG. 5). The compound 3-aminopropyltriethoxylsilane (APTES) is used in this example. This is a bifunctional reagent with an amino group on one end and the silane moiety on the other. Silanes covalently couple to glass and other surfaces through hydroxyl groups on the surface. These reagents have been used successfully for attachment of biomolecules to surfaces for examination by AFM (15). The general method is to prepare a volatile solution of the silanation reagent (e.g., 1% in ethanol) and place it in close proximity to the sample in a dessicator. The dessicator can be evacuated to enhance the process. The silane adsorbs to the surface and is cured by treating at 110° C. for several minutes or at room temperature overnight.

FIG. 5 schematically illustrates a strategy for covalent attachment of biomolecules to the tip. The tip is first modified with an aminosilane, leaving free primary amine groups on the surface. The biomolecules are then coupled to the amines via chemical condensation facilitated by a soluble carbodiimide such as EDAC. Since nucleic acids lack carboxyl groups, a variation of this approach using thiol-modified nucleic acids and aminosilanated tip surfaces is used.

After attachment of the APTES to the surface of the tip, biomolecules with carboxylic acid groups (e.g., proteins) are covalently coupled to the primary amine using a water soluble condensing reagent such as EDAC (FIG. 5). Coupling of nucleic acids is accomplished by the protocol described by Lee et al. (8). Oligonucleotides are synthesized by conventional phosphoramidite chemistry and a thiol group is added at either the 3' or 5' end. The thiolated oligonucleotides are then coupled to aminosilane modified tips surfaces using 4-(P-maleimidophenyl)butyrate. In the experiments performed by Lee et al., (8) biomolecules were attached to silica spheres which were then glued to cantilevers. Both direct attachment to the silicon nitride tips and to silica spheres is used, as described below.

Photon Induced Coupling

A method for photon induced coupling of biological samples to scanning tips is employed. Similar methods have been developed for immobilization of biomolecules over large areas (16). This approach has the significant advantage that the biomolecule to be attached will only be covalently bound at the sight of light activation. To accomplish this, the bifunctional reagent succinimidyl p-azidobenzoate, or a related compound is used. This reagent has a succinimide group at one end that will couple covalently to aminosilane treated tip surfaces. The other end is a azidobenzoic acid group that is converted to highly reactive intermediates upon irradiation with<360 nm light. Following modification of the tip with the aminosilane-succinimidyl-azidobenzoate compounds, the tip is treated with highly focused UV light from an argon ion laser as follows. The modified tip is immersed in a solution of the biomolecule of interest and irradiated with a small spot of UV light focused on the apex region of the tip. This activates the azidobenzoate group, forming a highly reactive nitrene, and leads to coupling of biomolecules in the activated domain. Time course, concentration, and UV dosage experiments are carried out to determine the optimal conditions for attachment of proteins to the activated domain of the tip. Attachment is assayed as described below. An alternative method is to use an alkanethiolate terminating with the azidobenzoate group to produce a photoactive surface on gold coated tips. As mentioned above, this allows coupling of biomolecules to the tip rather than to the entire cantilever as is currently the case using chemical coupling methods.

Figure 6:
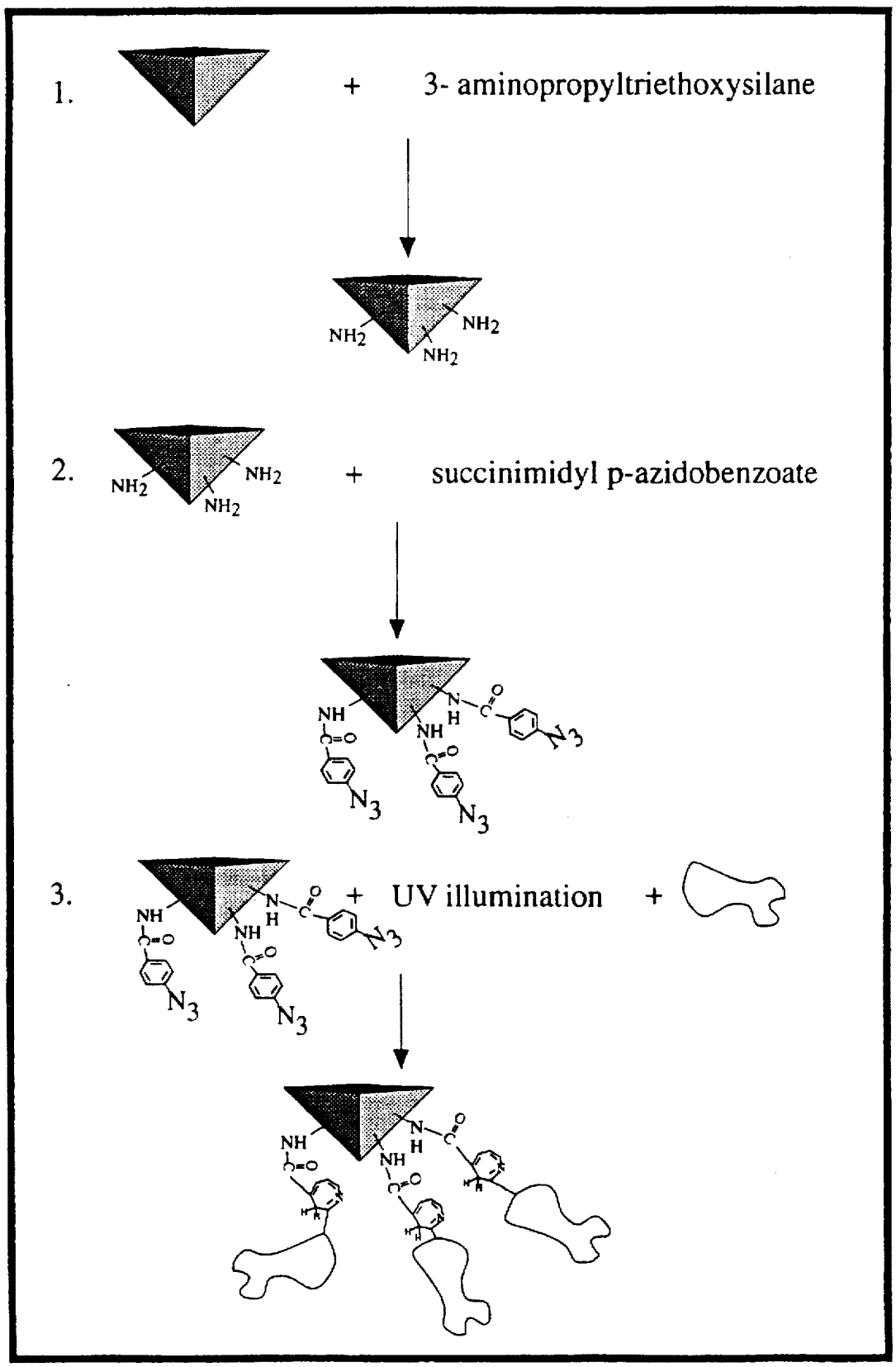
FIG. 6 is a schematic illustrating photon induced coupling of biomolecules to scanning tips.

FIG. 6 schematically illustrates photon induced coupling of biomolecules to scanning tips. In this strategy, a photoactivatable group (azidobenzoate) is coupled to an aminosilane modified tip. In the presence of the desired biomolecule, the tip is irradiated with UV light (~355 nm) which activates the azidobenzoate moiety and leads to covalent attachment through primary amines on the biomolecule. For DNA, 5' and/or 3' amino modified DNA is used since aromatic amines are usually less reactive than primary amines.

Particle Mediated Attachment

Figure 7:
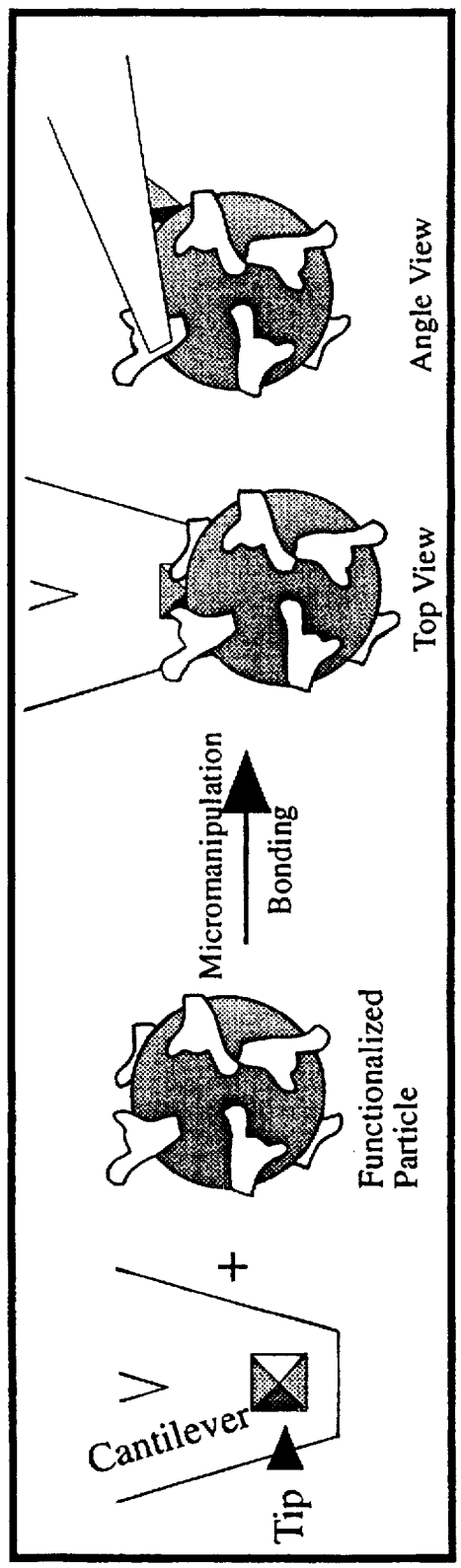
FIG. 7 is a schematic showing the method of bonding particles with biomolecular surfaces to cantilevers.
Figure 8:
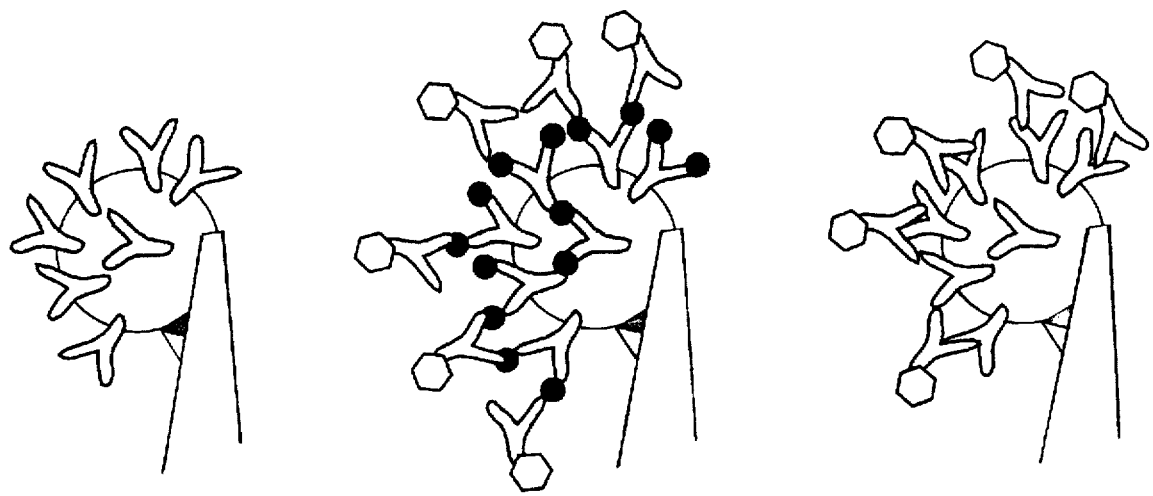
FIG. 8 is a plan view of a scanning tip showing a fluorescent assay method.
Figure 8:
Figure 8:

A second approach to tip modification is to attach functionalized particles to tips. Depending on the experimental strategy, the microparticles are either attached prior to coupling to biomolecules, or coupled to biomolecules and then attached to the cantilever. Molecules with free amine groups are attached to carboxylate or aldehyde modified spheres using a condensing reagent such as EDAC as described in the previous section. Microparticles are chosen that are larger in diameter than the height of the existing tip (~4 microns) so that there is no interaction between the pyramidal tip and the substrate (FIGS. 7 & 8). The particles are attached directly to the tips or to cantilevers, adjacent to the existing tip. In some cases, tip-less cantilevers are used, facilitating use of smaller (<4 micron dia.) microparticles. The microparticles are manipulated into place using a mechanical micromanipulator, laser trap, or other manipulation tool, and bonded using epoxy or a similar reagent. In some cases, the particles are bonded using heat (e.g., from an infrared laser source) or UV light in conjunction with a UV curable epoxy.

Figure 10A:
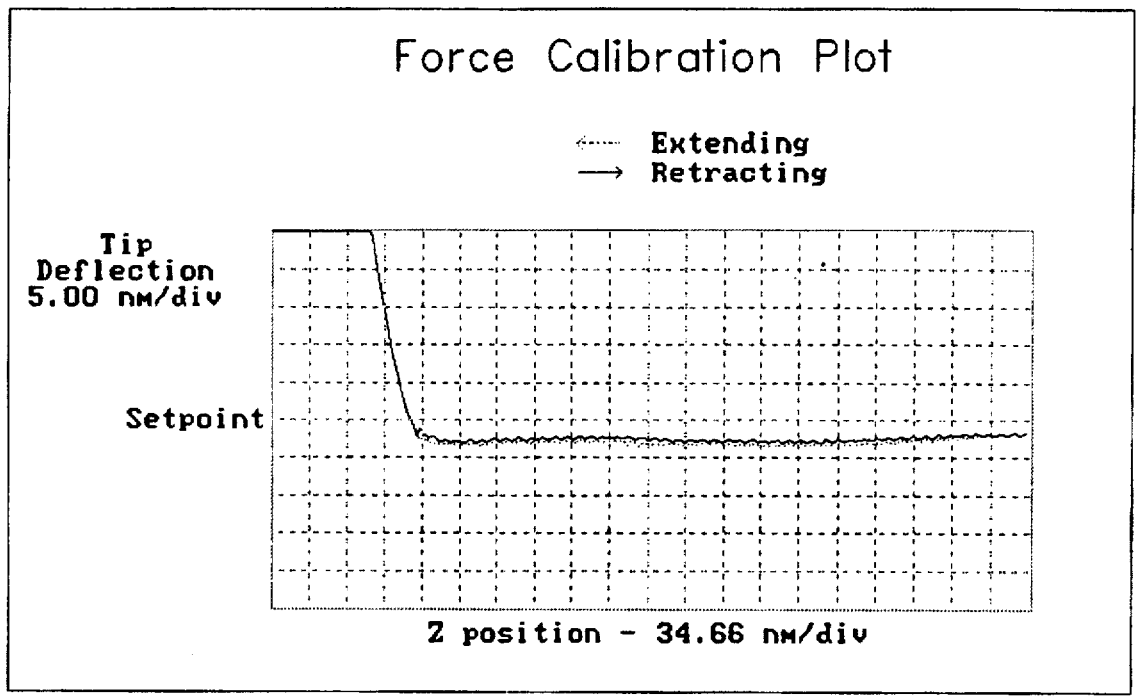
FIG. 10A is a force curve analysis with a BioTip, that is, a biologically active modified tip. The tip is modified with an antibody made in goats (GAB) and reactive with a rabbit antibody (RAB). In the top panel the force curve represents the adhesion between the GAB BioTip and a GAB surface in the absence of the antigen RAB; and the bottom panel shows the resulting adhesive spike (arrow) that occurs upon addition of the RAB antigen.
Figure 10A:
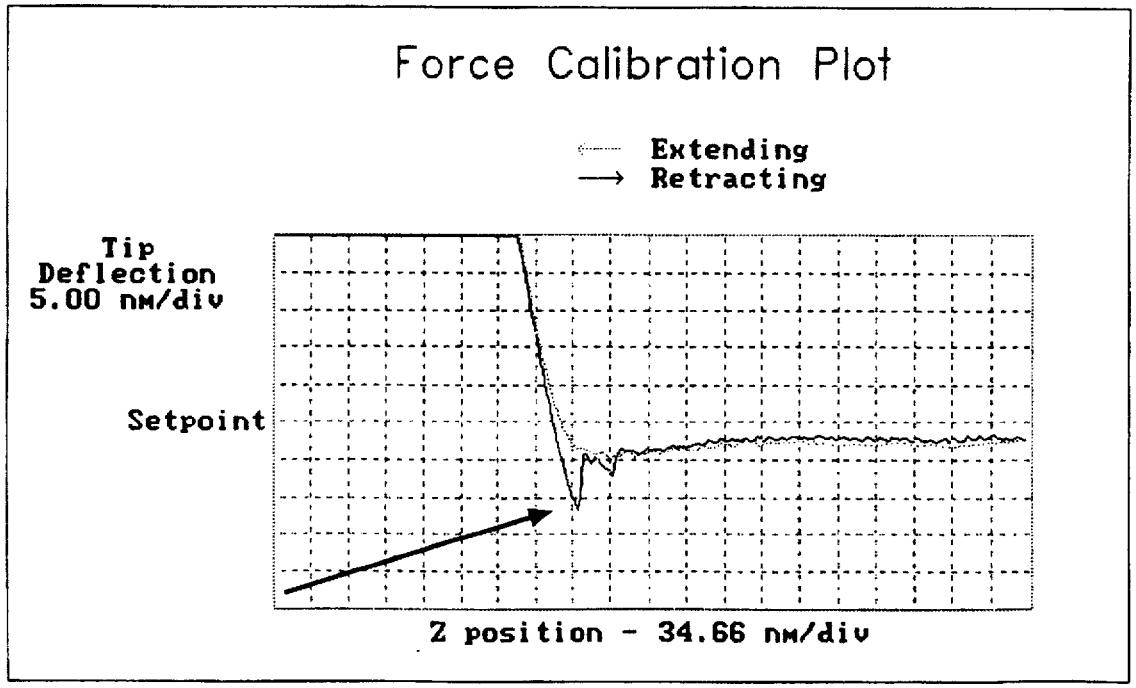

Tips constructed in this fashion have been used for molecular force detection experiments in an antibody sandwich assay (FIG. 10A: see below). The tips performed well. Artifactual stick-slip interactions were largely overcome by using a minimal contact force curve strategy (17).

FIG. 7 schematically illustrates the method used to bond particles with biomolecular surfaces to cantilevers. FIG. 8, left and middle panels are light micrographs of a modified scanning probe created by this method.

Tip Modification Efficiency

To assess the efficiency of the various protocols for attachment of biomolecules to tips the following methods are employed. For APTES modified surfaces, the tips are reacted with either FITC or TRITC (fluorescein and rhodamine isothiocyanate, respectively) which couples to samples with primary amines at basic pH. The fluorescence of the tips in experiment and control samples is measured and quantitated optically using a fluorescence microscope equipped with an integrating CCD camera and associated computer hardware and software. To assay protein attachment, tips are treated with fluorophore-conjugated antibodies to the proteins. The level of fluorescence in control and experimental samples is determined and quantitated.

FIG. 8 illustrates the assay for tip modification efficiency. In this case the modified scanning probe in the middle panel was modified with an antibody and its presence detected by a fluorescent secondary antibody (right panel). To ensure biological activity of the primary antibody, a fluorescent antigen is used in a similar fashion.

In these experiments, the tips are pretreated with a "blocking" protein to bind all non-specific reaction sites and minimize background binding of the fluorochrome modified antibody. To assess the efficiency of binding of DNA to tips, the tips are treated with trace amounts of $32_p$ labeled DNA during the binding reaction. The radioactive modified scanning probes are placed in a PhosphorImager or scintillation counter and the disintegrations of the $32_p$ label are counted as a function of time. A second approach for quantitation of DNA binding is to use a fluorescent DNA binding molecule, (e.g., YOYO-1 for single stranded DNA, ethidium homodimer I for double stranded DNA). Experimental and control tips are treated with the fluorescent dyes and the fluorescent yield quantitated as described above.

Assaying the efficiency of tip modification by the passive adsorption or the covalent attachment protocols is somewhat problematic because these methods modify the entire surface of the tip and the cantilever on which it is positioned. Thus, the assays described provide only qualitative assessments of the utility of the modification procedure. Tips modified by the photon induced coupling method are only functionalized in the region irradiated with UV light. Ability to focus the UV laser to<2 microns results in covalent attachment of biomolecules limited to the tip apex, allowing a more quantitative evaluation of the modification efficiency.

For additional quality control, both SEM and TEM are used to examine functionalized tips and obtain a qualitative assessment of the change in tip morphology as a consequence of the modification processes. Tips that look promising based on the analyses described above are tested in force detection assays.

Substrate Modification

As with tips, substrates are prepared by several different methods. These methods are the same as those used to modify tips, i.e., covalent attachment via bifunctional silanes, and photon induced coupling. In most cases glass or mica surfaces are used.

The methods of choice are as follows:
Gold/Alkanethiolate Surfaces

Using gold coated surfaces biomolecules are chemically coupled as described for attachment to gold coated tips. This method has worked well, providing a stable and uniformly coated surface.

A successful alternative substrate preparation method has been to deposit particles with the desired biomolecular surface on glass or Cel-Tak coated glass. Formation of stable arrays occurs at high particle density. At lower densities, the use of epoxy or Cel-Tak facilitates particle adsorption and stability. Particles deposited in this way have proven stable enough to allow force detection experiments to be carried out.

A third approach that has worked is to use two modified scanning probes that are aligned so that the functionalized tip on one contacts the functionalized tip on the other. This arrangement is facilitated by optical alignment using a combined optical/atomic force microscope. By using cantilever pairs with one low and one high spring constant, and careful optical monitoring of the experiment, artifactual force phenomena, such as the stick-slip mentioned above, are minimized.

The gold/alkanethiolate and APTES methods are readily integrated with the concept of a photoactivatable surface as described above (succinimide p-azidobenzoate). A focused UV laser beam is used to activate only small domains of the surface while it is immersed in a solution of the biomolecule of interest. The activated domains react with the biomolecule. This is followed by extensive washing and characterization of the degree of binding by AFM and EM analyses. Again, this methodology for sample deposition in ordered arrays is useful in designing diagnostic tests based on force interaction assays using modified scanning probes.

EVALUATION OF MODIFIED TIPS

Detecting Molecular Interactions Using Functionalized Probes

As described earlier, three approaches are used to assess the ability of functionalized probes to detect specific molecular interactions. Two of these approaches have been described in the prior art. These are: pull-off force measurements (adhesion) and lateral force measurements (friction). The third approach is a novel component of this application. It is detection and measurement of changes in resonant properties of the modified probe. These properties include amplitude, frequency, and/or phase. All of these methods are applied to samples in solution. There are two reasons for this. First, most diagnostic assays involving biomolecular detection are performed on molecules in their native state in solution since non-native conditions often disrupt biologically relevant interactions. Second, in air, binding forces between the scanning tip and the sample are dominated by strong interactions between thin surface layers of water. Thus, even if molecules were able to function under these conditions, the signal to noise would be insufficient to detect these interactions.

Pull-off Force Measurement

Figure 9:
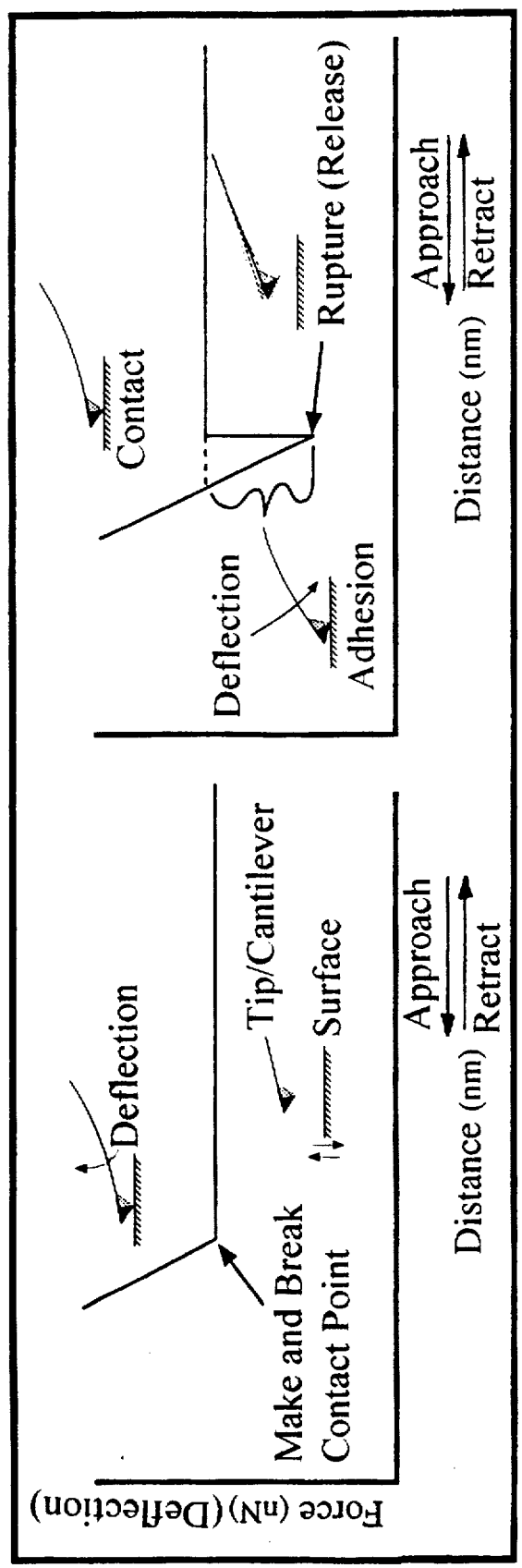
FIG. 9 is a set of graphs illustrating pull-off force ("force curve") measurement.

FIG. 9 graphically illustrates the pull-off force measurement. The figure shows a Force vs. Distance curve as the sample and tip are moved relative to each other. The tip is engaged with the surface, then pulled away. Due to adhesion between the tip and the surface, the cantilever is bent until the adhesive bond ruptures, allowing the tip to return to the zero deflection point. The bonding force is thereby measured, providing a direct assessment of the interaction between biomolecules on the tip and on the surface.

Figure 2:
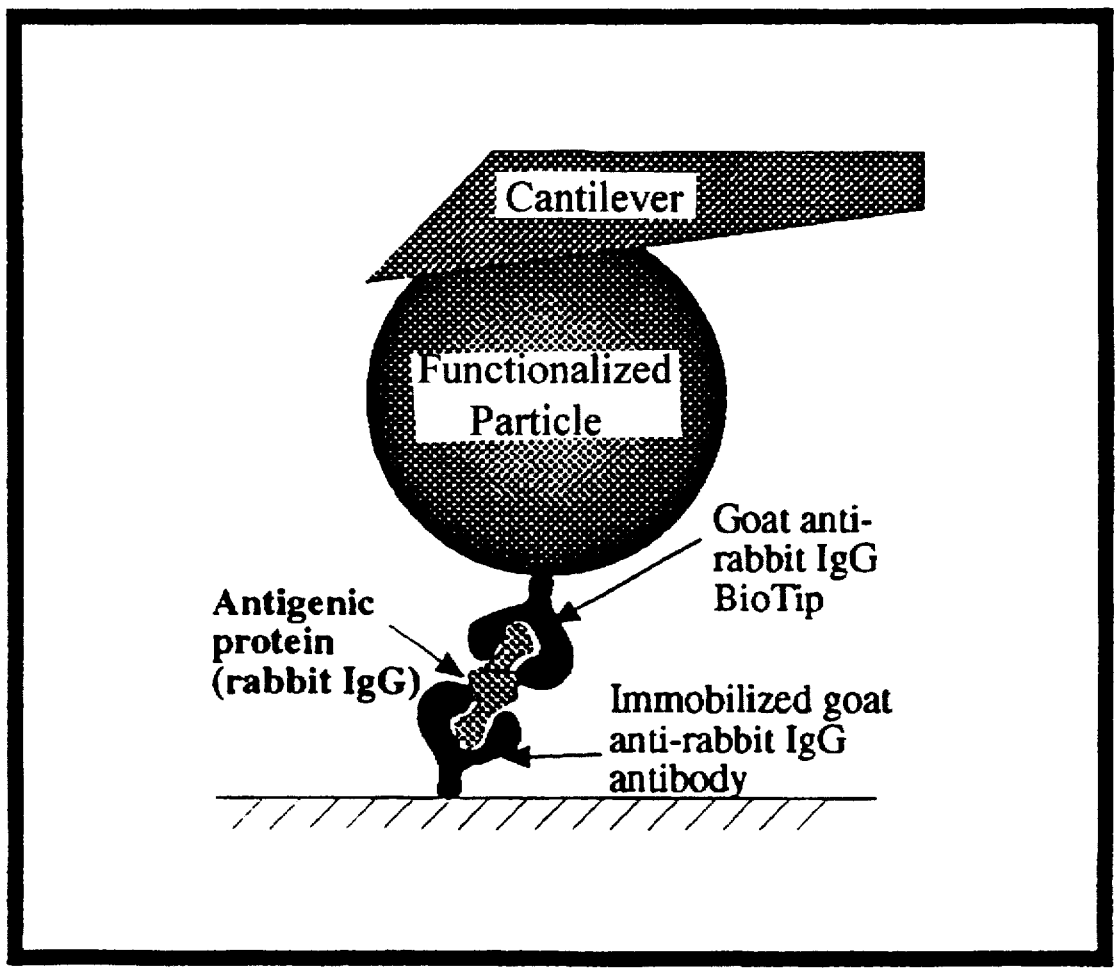
FIG. 2 is a schematic showing the interaction between functionalized scanning tips and surface immobilized biomolecules.

We have used this approach to measure the adhesive force between modified scanning probes and a specific substrate. For example, FIG. 2 shows an antibody sandwich assay in which the antigen is trapped between an antibody on a surface and on a modified scanning probe. This assay has been successfully used with both gold alkanethiolate modified scanning probes and particle modified scanning probes. Data from these experiments are presented in FIGS. 10A and 10B.

Figure 10B:
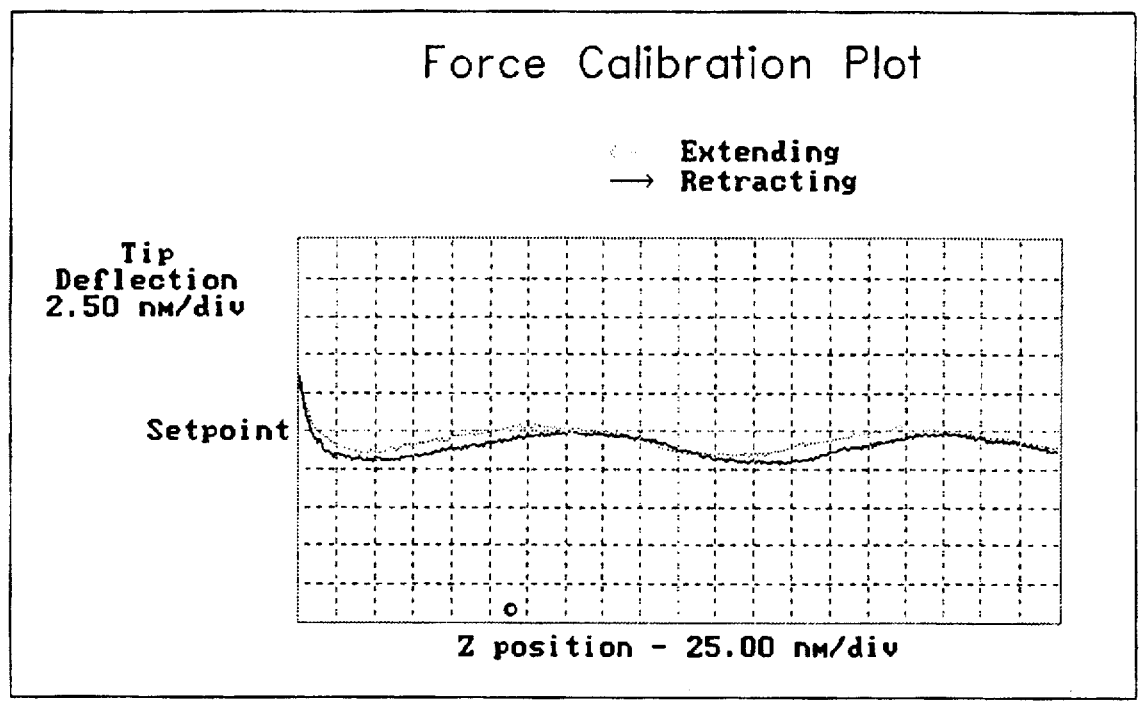
FIG. 10B is a force curve analysis with a gold alkanethiolate BioTip coupled to GAB. In the top panel the force curve represents the adhesion between the alkanethiolate GAB BioTip and a GAB surface in the absence of the antigen RAB; and the bottom panel shows the resulting adhesive spike (arrow) that occurs upon addition to the RAB antigen.
Figure 10B:
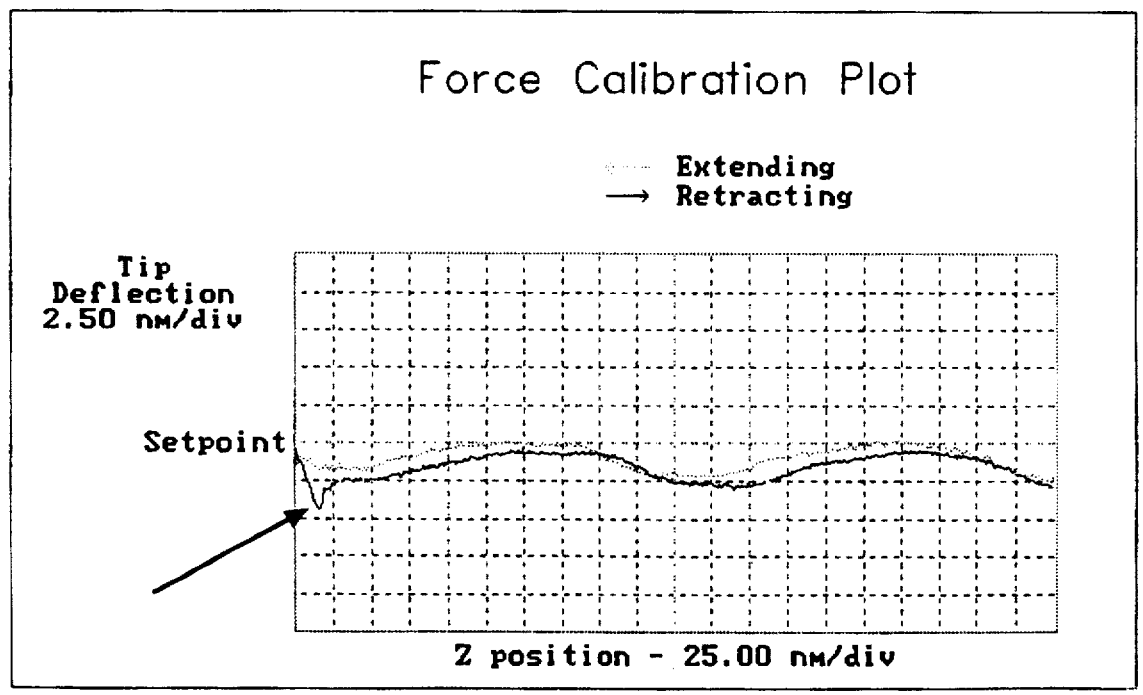

FIGS. 10A and 10B illustrate a molecular force antibody sandwich assay. FIGS. 10A and 10B show molecular force measurement data from antibody sandwich assays (FIG. 2) using functionalized AFM probes constructed by the microparticle method (FIG. 10A) or the alkanethiolate method (FIG. 10B). The top panel in 10A and 10B shows the force curve obtained in the control experiment lacking the antigenic molecule. The bottom panel in 10A and 10B shows the experimental data in the presence of the antigen. Note the diagnostic adhesion spike in the lower panels, indicative of a defined antibody-antigen interaction. The low frequency oscillation seen in FIG. 10B is the result of optical interference in the optical detection system and does not effect the molecular force measurement.

In previous studies, it was suggested that soft surfaces are better for this type of experiment because they accommodate lateral tip motion and tip-induced sample compression (5). In contrast, hard glass spheres worked well for measuring DNA/DNA interactions in some experiments (8). Therefore, both modified glass surfaces and soft agarose beads are used as the test substrates. Major emphasis is placed on discrimination between non-specific and specific molecular interactions. This issue has not been completely addressed in the pioneering work in the literature, but it is critical for the commercialization of molecular force detection technology. To accomplish this task, appropriate negative controls are incorporated in all experiments and statistical methods are used to evaluate the significance of interaction events observed (e.g., comparing the average number of binding events in experimental and control samples at numerous locations on the sample surface).

An advantage of the pull-off force approach is that measurement of vertical cantilever deflection is extremely sensitive, permitting detection of sub-nanoNewton (nN= $10^{-9}$ Newton), possibly sub-picoNewton (pN=$10^{-12}$ Newton), forces. There are, however, several disadvantages of pull-off force measurements. First, there is significant lateral motion of the tip when it engages and disengages the surface (18). This sliding motion can disrupt molecular interactions and confuse interpretation of the pull-off force data. Second, the repeated forceful interaction of the tip with the surface can cause degradation in tip performance. Finally, usually one spot on the surface is sampled many times in a given experiment, making a statistical comparison of many experiments necessary to validate data interpretation. Therefore, although pull-off force measurements have been successful in some cases, other methods are explored as well.

Figure 14:
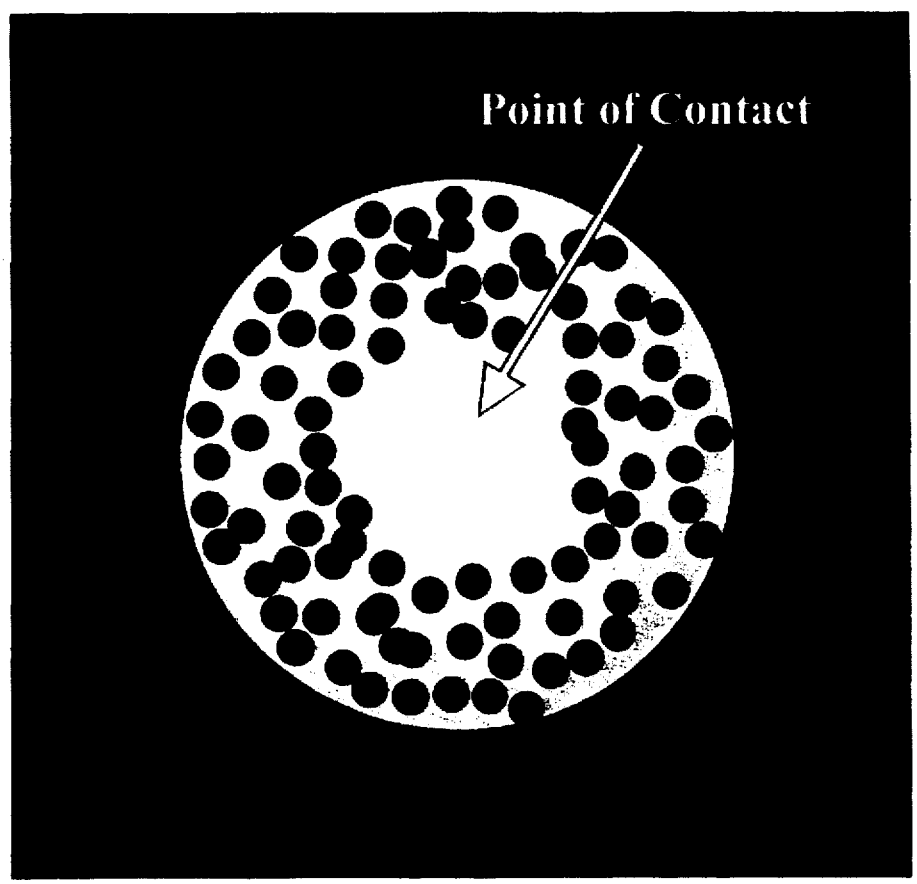
FIG. 14 is an image of an antibody particle BioTip after use in a force curve assay. The light areas are fluorescent domains that indicate maintenance of biological activity. The dark spot at the tip apex illustrates how a conventional force curve assay can destroy biological activity due to unnecessary high forces during molecular detection cycles.

FIG. 14 shows a tip assayed by a fluorescence method after use in force curve analyses. The dark spot at the tip apex is a clear indication of tip degradation at the point of contact between the tip and the sample.

Lateral Force Measurement

This type of measurement has been used successfully to detect differences in force interactions between chemically modified tips and surfaces (11) and to identify frictional domains in thin films (19). In this method, torsion on the cantilever is generated as the tip interacts with the surface during a lateral scan (FIG. 11). The degree of torsion is proportional to the strength of the interaction. Therefore, non-specific (weak) and specific (strong) interactions can be distinguished. Moreover, one can measure friction and topography simultaneously, providing independent data sets that could aid in detection of particular interaction types. Although the sensitivity of this method may be lower than that of the pull-off method, its potential for scanning arrays of molecules make it attractive for solid phase diagnostics.

To carry out these experiments, functionalized tips are scanned over modified surfaces described above. Surface arrays of specific and non-specific substrates are particularly informative since different frictional domains are observed as has been reported for thin films (19). Lateral deflection of the tips is monitored and correlated with the location of the tip on the sample. Functionalized tips give the greatest lateral force signal when scanned over a domain containing the appropriate complementary molecule.

FIG. 11 schematically illustrates detection of tip/surface interactions using lateral force measurements. In the end view (the long axis of the cantilever is perpendicular to the plane of the paper) the tip is subject to torsional motion due to friction between it and the surface. This friction should be greater when there is a specific biomolecular interaction between a functionalized tip and the appropriate molecule on the surface.

Resonance Methods
Amplitude Frequency and/or Phase Shift Measurement

Methods for image acquisition using a scanning tip vibrating at or near a resonance frequency have been developed (TappingMode) (20, 21). These methods have even more recently been extended to operate in solution (20, 22). In this mode, the scanning tip makes transient contact with the surface, "sampling" each position many times. While the prior art suggests the applicability of pull-off and lateral force approaches for molecular detection, tapping mode has not been evaluated in this context. Interactions between a rapidly oscillating tip and a specific surface cause amplitude, frequency, and/or phase shifts in the resonating tip will allow detection of specific biomolecular interactions (FIG. 12).

In solution, tips are typically resonated between 8 and 16 kHz although frequencies in excess of 300 kHz can be used for image acquisition. As the tip approaches the surface of interest, force interactions cause a reduction in resonance amplitude and this is used to generate image contrast. These forces are much lower than those used in contact mode scanning procedures, and they have a negligible lateral component, which can compromise sample integrity and stability in some cases. In practice, the tip is resonated and brought to the surface of interest. Light or no contact is established (i.e., tapping). Then the tip is scanned over the surface, passing over domains of specific and non-specific interactions, as described above. Increased interaction forces that occur when the tip interacts specifically with the surface causes a reduction in amplitude, a change in resonance frequency, and/or a shift in the phase relationship between the signal being used to drive the modified scanning probes and the signal being detected from the oscillating cantilever. These changes are sufficient to reliably detect specific interactions between the molecular species on the tip and on the surface.

Figure 12:
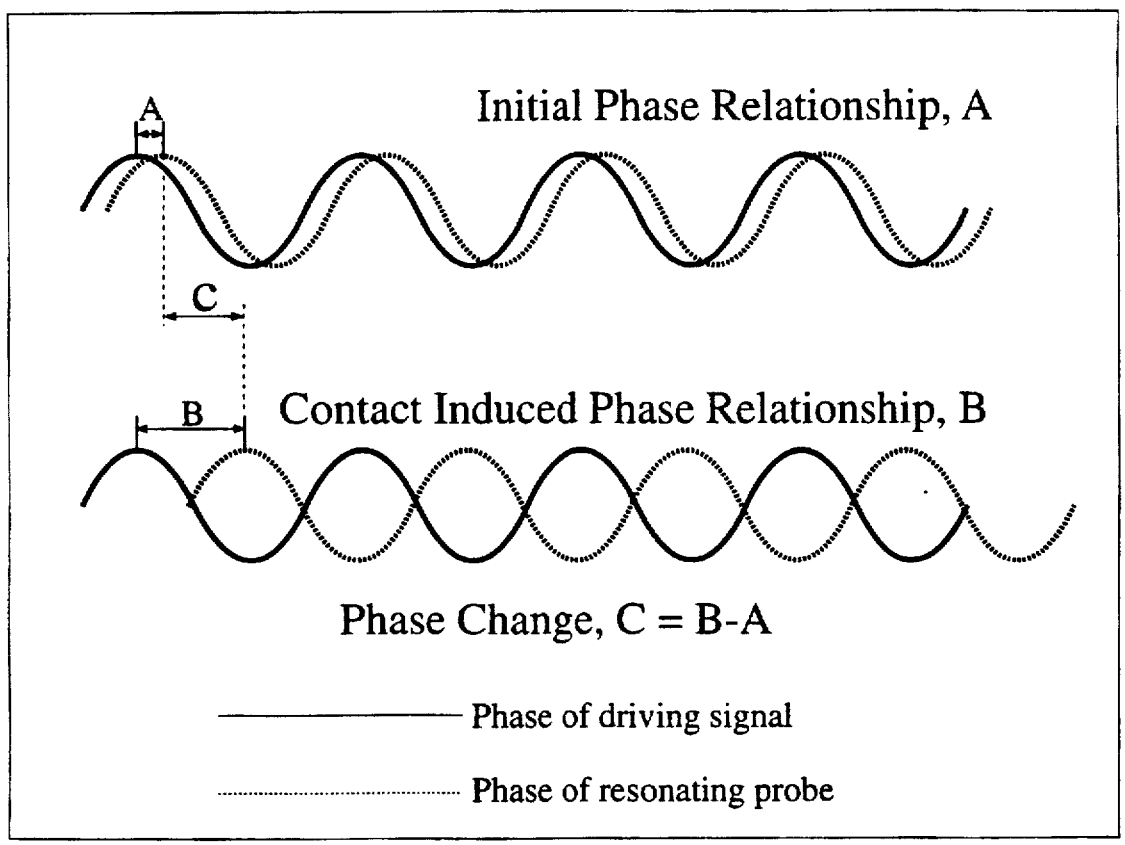
FIG. 12 is a schematic showing phase shifting.

FIG. 12 graphically shows the detection of interactions between functionalized tips and surfaces by monitoring changes in the resonance properties of the oscillating modified scanning probes as it interacts with the surface. In this scenario, when the tip interacts with a specific substrate the increase in binding force will cause a shift in resonance frequency. Resonance amplitude and phase are also monitored.

Figure 13:
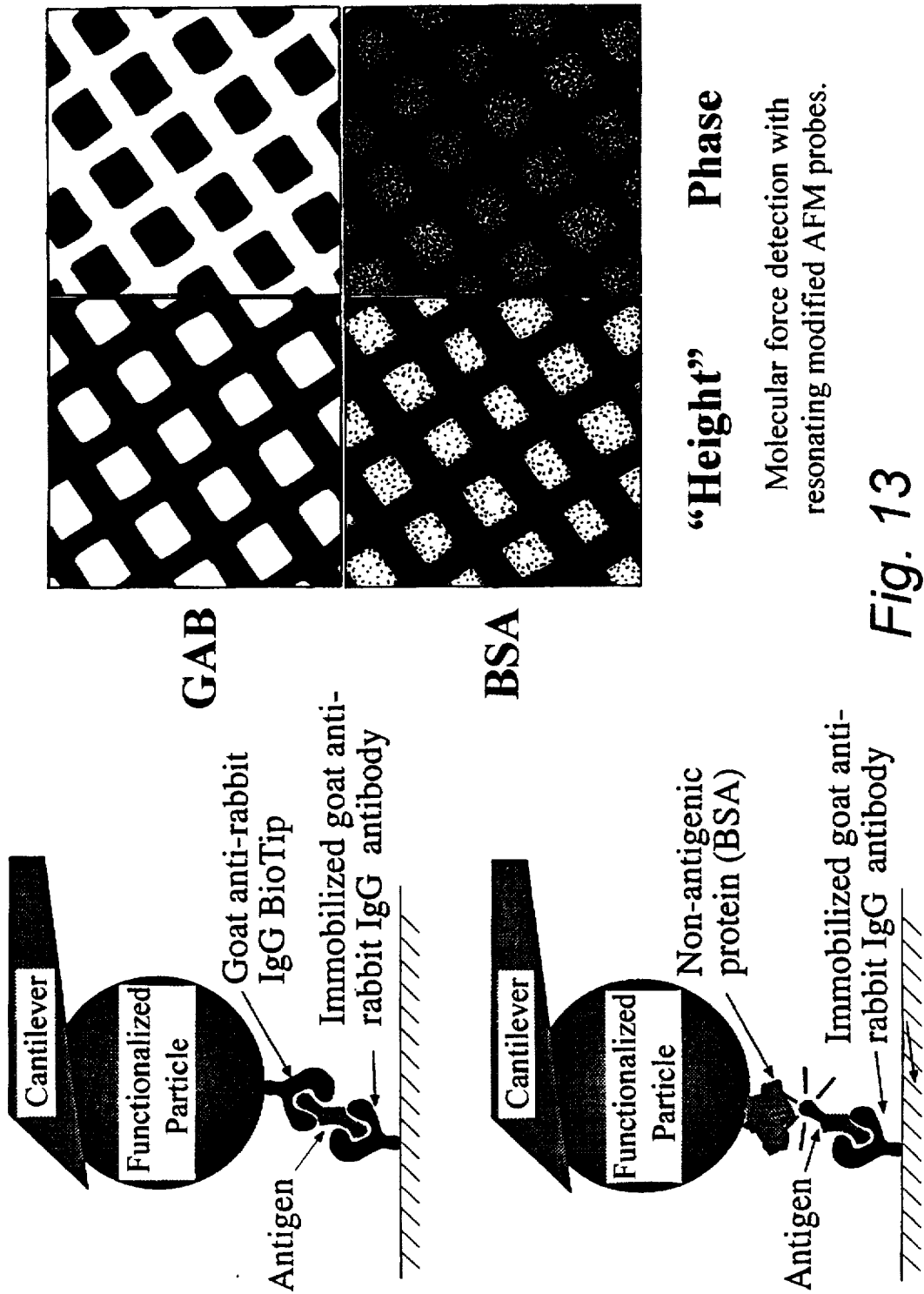
FIG. 13 is a schematic illustrating molecular force detection with resonating modified AFM probes.

FIG. 13 shows an example of a resonance-based molecular detection experiment. The experimental system is the antibody sandwich described earlier. The sample surface has been coated with antibodies in specific domains, each a square approximately 7 microns wide. The antibodies on the surface were bound to the appropriate antigen. The modified resonating probe was brought into light contact with the patterned surface and scanned. The amplitude and phase parameters were monitored. The amplitude parameter was used in the feed back loop to regulate the degree of transient contact between the resonating probe and the surface. The phase parameter was monitored to detect changes in adhesion between the probe and the surface. In the top two panels, the amplitude and phase data are shown for scans using an antibody-modified resonating probe. The bottom two panels show the identical experiment, but in the presence of a resonating probe modified with a non-specific protein (bovine serum albumin: BSA) that does not interact strongly with the antibody/antigen complex on the surface. The scales are the same in both the experimental and control samples. Therefore, the antibody modified resonating probe showed a clear affinity for the antibody/antigen complexes on the surface, relative to the minor, non-specific binding observed with the BSA modified probe. These data demonstrate that resonating probes with a particular biological functionality can be used to detect and/or measure interactions with biomolecular substrates. This example can be extended to include chemical and material substrates as well.

EXAMPLE 1

Particle BioTips

Carboxyl Coated Latex Microspheres (5.6 um, 7 um, 9 um)
Covalent coupling of proteins to carboxylate-modified latex 1. The selected protein for coupling is dissolved or diluted in MES buffer (27 ug/100 ul) in a 1.5 or 0.5 ml microfuge tube.
2. Beads in aqueous suspension are added to give 0.5% solids at final concentration.
3. Beads and protein in MES are incubated at room temp. for 15 minutes.
4. 200 ug EDAC/100 ul reaction volume is added.
5. Reaction is mixed by inversion and/or vortexing.
6. pH is adjusted to 6.5/O 0.2 with dilute NaOH (not usually necessary).
7. Reaction is incubated on rotating/orbital wheel for 2 hr-overnight.
8. Add glycine to give 100 mM in final rxn
9. Incubate 30–60 min.
10. Wash beads by centrifugation, removal of supernate, and resuspend in 50 mM PBS.
11. Repeat step 10 two more times.

MES buffer is 50 mM at pH 6.0
EDAC [1-ethyl-3-(3-dimethylaminopropyl)-carbodiimide] is reaction grade 1. Add 160 ul MES to 0.5 ul microfuge tubes.
2. Add 5 ul of Goat anti Rabbit IgG (Stock-10 ug/ul) to give 50 ug/200 ul final rxn.
3. Add 10 ul latex spheres (Stock=10% solids) to give 0.5% solids final rxn
   note: stock solution changes in concentrations compensated by MES volume
4. Incubate 15 min. In separate tube, add 50 ul MES and 400 ug EDAC
5. Add 25 ul MES+EDAC solution to rxn.
6. Check pH, should be 6.5 O 0.2
7. Incubate 2 hrs–12 hrs
8. 50 ul of a 500 mM glycine stock is added to rxn (100 mM final gly concentration)
9. Incubated 30–60 min.
10. Wash beads by centrifugation (5 sec.), remove supernatant, and resuspend in 50 mM PBS
11. Repeat step 10 two more times MES is actually ~54 mM at pH 6.0 to compensate for its dilution

EXAMPLE 2

Gold BioTips
Alkanethiolate Carboxylate Coated Gold
   covalent binding of proteins to carboxylated alkanethiolate coupled to gold 1. AFM tips are placed in Ion Beam sputter attached to sample holder
2. Tips are coated with 30 nm Au/gold while sample stage rotates
3. Tips are stored under vacuum until needed
4. Tips are secured to a microfuge tube polypropylene insert via No. 4 Gel Pak™
5. Tips are placed in 1.5 microfuge tube containing 1–2 mM alkanethiolate in 100% EtOH
6. Tips are incubated 24 hrs at 4˚C. (may be incubated longer)
7. Tips are rinsed with 50 mM PBS (this is done by displacement of the thiol acid solution by a steady stream of fresh PBS into the microfuge tube)
8. Tips are next removed from PBS and placed in MES
9. The selected protein for coupling is added (27 ug/100 ul MES)
10. Tips and protein in MES are incubated at room temp. for 15 minutes.
11. 200 ug EDAC/100 ul reaction volume is added.
12. Reaction is mixed by inversion and/or vortexing.
13. pH is adjusted to 6.5 O 0.2 with dilute NaOH (not usually necessary).
14. Reaction is incubated on rotating/orbital wheel for 2 hr-overnight.
15. Glycine added to give 100 mM in final rxn
16: Incubated 30–60 min.
17. Tips are washed by displacement with a steady 50 mM PBS flow

EXAMPLE 3

Resonance Based Detection of Antibody Sandwich formation

1. A goat anti-rabbit IgG antibody (GAB) is immobilized on a gold surface as described in Example 2. The GAB antibody is attached to a gold coated probe in a similar fashion.
2. The modified tip and surface are positioned in an AFM capable of making resonance measurements.
3. The modified tip is scanned over the surface which contains both GAB domains and domains that are devoid of the GAB antibody (i.e., a patterned surface). Interactions are measured by monitoring changes in resonance amplitude, frequency, and phase. Subsequently, the antigen, a rabbit antibody (RAB) is titrated into the reaction space. The concentration range is between 1 nM to 1 mM. The RAB becomes trapped between the tip and surface-bound antibodies, forming a trimolecular complex. This increases the adhesion between the tip and surface, changing the resonance parameters.
4. A change in contrast in observed as a function of formation of the trimolecular antibody sandwich which results in increased adhesion.

5. A control experiment is carried that is identical to that for that described thus far in this example except that the probe does not contain the GAB antibody. Instead, it is coupled to a non-specific protein, bovine serum albumin (BSA). This protein fails to bind to the RAB antigen. There is little or no change in the resonance parameters due to the lack of change in adhesion in this control experiment.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

APPENDIX

1. G. Binnig, H. Rohrer, C. Gerber, E. Weibel, *Phys. Rev. Lett.* 49, 57–61 (1982).
2. S. Alexander, *J. Appl. Phys* 65, 164–167 (1989).
3. B. Drake, et al., *Science* 243, 1586–1589 (1989).
4. G. Meyer, N. M. Amer, *Appl. Phys. Lett.* 53, 1045–1047 (1988).
5. E.-L. Florin, V. T. Moy, H. E. Gaub, *Science* 264, 415–417 (1994).
6. J. H. Hoh, P. E. Hillner, P. K. Hansma, *Proc. Micro. Soc. America* 52, 1054–1055 (1994).
7. V. T. Moy, E.-L. Florin, H. E. Gaub, *Science* 266, 257–259 (1994).
8. G. U. Lee, L. A. Chrisey, R. J. Colton, *Science* 266, 771–773 (1994).
9. T. Boland, B. D. Ratner, *Proc. Natl. Acad Sci. USA* 92, 5297–5301 (1995).
10. P. Hinterdorfer, W. Baumgartner, H. J. Gruber, K. Schilcher, H. Schindler, *Proc. Natl. Acad. Sci.* 93, 3477–3481 (1996).
11. C. D. Frisbie, L. F. Rozsnyai, A. Noy, M. S. Wrighton, C. M. Lieber, *Science* 265, 2071–2074 (1994).
12. A. Noy, C. D. Frisbie, L. F. Roznyai, M. S. Wrighton, C. M. Lieber, *J. Am. Chem. Soc.* 117, 7943–7951 (1995).
13. J.-B. D. Green, M. T. McDermott, M. D. Porter, *J. Phys. Chem.* 99, 10960–10965 (1995).
14. J. H. Hoh, J. P. Cleveland, C. B. Prater, J.-P. Revel, P. K. Hansma, *J. Am. Chem Soc.* 114, 4917–4918 (1992).
15. Y. L. Lyubchenko, S. M. Lindsay, J. A. DeRose, T. Thundat, *J. Vac. Sci. Technol. B* 9, 1288–1290 (1991).
16. S. Karrasch, M. Dolder, F. Schabert, J. Ramsden, A. Engel, *Biophys. J.* 65, 2437–2446 (1993).
17. J. K. Stuart, V. Hlady, *Langmuir* 11, 1368–1374 (1995).
18. J. H. Hoh, A. Engel, *Langmuir* 9, 3310–3312 (1993).
19. R. M. Overney, et al., *Nature* 359, 133–135 (1992).
20. P. K. Hansma, et al., *Appl. Phys. Lett.* 64, 1738–1740 (1994).
21. Q. Zhong, D. Inniss, K. Kjoller, V. B. Elings, *Surf. Sci. Lett.* 290, 688–692 (1993).
22. C. A. J. Putman, *Appl. Phys. Lett* 64, 2454–2456 (1994).

We claim:

1. A method of analyzing for the presence of a specific material in a sample using a sensor including a resonating member having a probe and a known material disposed on or forming the probe, the sensor having resonance properties, the method comprising the steps of:

positioning the sensor proximate to the sample;

detecting a force dependent change in the resonance properties of the sensor resulting from the positioning step;

confirming the presence of the specific material in the sample based on the identity of the known material and the detection of a resonance change; and determining the concentration of the specific material in the sample based on a rate and degree of change in the resonance properties of the sensor when the sensor and the sample are maintained in proximate relationship.

2. The method of claim 1 further including the step of:
   determining a binding energy between the known material and the specific material based on the magnitude of the force dependent change in the resonance properties of the sensor.

3. The method of claim 1 wherein the detecting step includes detecting the change in amplitude of the sensor.

4. The method of claim 1 wherein the detecting step includes detecting the change in frequency of the sensor.

5. The method of claim 1 wherein the detecting step includes detecting the change in phase of the resonance signal of the sensor.

6. The method of claim 1 wherein the known material has a specific chemical function.

7. The method of claim 6 wherein the known material includes a carboxyl group.

8. The method of claim 6 wherein the known material includes an amino group.

9. The method of claim 6 wherein the known material includes a succinimide group.

10. The method of claim 6 wherein the known material includes an aryl azide group.

11. The method of claim 6 wherein the known material is a biomolecule selected from a group consisting of DNA, RNA, ad protein.

12. The method of claim 6 wherein the known material includes an antibody.

13. A method of analyzing for the presence of a specific material in a sample using a sensor including a resonating member having a probe and a known material disposed on or forming the probe, the sensor having resonance properties, the method comprising the steps of:

positioning the sensor proximate to the sample;

detecting a force dependent change in the resonance properties of the sensor resulting from the positioning step;

confirming the presence of the specific material in the sample based on the identity of the known material and the detection of a resonance change; and determining a binding energy between the known material and the specific material based on the magnitude of the force dependent change in the resonance properties of the sensor.

14. The method of claim 13 wherein the detecting step includes detecting the change in amplitude of the sensor.

15. The method of claim 13 wherein the detecting step includes detecting the change in frequency of the sensor.

16. The method of claim 13 wherein the detecting step includes detecting the change in phase of the resonance signal of the sensor.

17. The method of claim 13 wherein the known material has a specific chemical function.

18. The method of claim 17 wherein the known material includes a carboxyl group.

19. The method of claim 17 wherein the known material includes an amino group.

20. The method of claim 17 wherein the know material includes a succinimide group.

21. The method of claim 17 wherein the know material includes an aryl azide group.

22. The method of claim 17 wherein the know material is a biomolecule selected from a group consisting of DNA, RNA, and protein.

23. The method of claim 17 wherein the known material includes an antibody.

24. A method of analyzing for the presence of a specific material in a sample using a sensor including a resonating member having a probe and a known material disposed on or forming the probe, the sensor having resonance properties, the method comprising the steps of:

positioning the sensor proximate to the sample;

detecting a force dependent change in the resonance properties of the sensor resulting from the positioning step; and confirming the presence of the specific material in the sample based on the identity of the known material and the detection of a resonance change, wherein the known material has a specific chemical function, and wherein the known material includes a succinimide group.

25. A method of analyzing for the presence of a specific material in a sample using a sensor including a resonating member having a probe and a known material disposed on or forming the probe, the sensor having resonance properties, the method comprising the steps of:

positioning the sensor proximate to the sample;

detecting a force dependent change in the resonance properties of the sensor resulting from the positioning step; and confirming the presence of the specific material in the sample based on the identity of the known material and the detection of a resonance change, wherein the known material has a specific chemical function, and wherein the known material includes an aryl azide group.

* * * * *